(12) United States Patent
Negishi et al.

(10) Patent No.: US 6,187,948 B1
(45) Date of Patent: Feb. 13, 2001

(54) FLUOROVINYL ETHER HAVING TERMINAL OXYGEN-CONTAINING FUNCTIONAL GROUP AND PROCESS FOR PREPARING THE SAME

(75) Inventors: Yoshio Negishi; Takayuki Araki; Tetsuo Shimizu, all of Settsu (JP)

(73) Assignee: Daikin Industries Ltd., Osaka-fu (JP)

( * ) Notice: Under 35 U.S.C. 154(b), the term of this patent shall be extended for 0 days.

(21) Appl. No.: 09/115,755

(22) Filed: Jul. 15, 1998

(30) Foreign Application Priority Data

Jul. 15, 1997 (JP) .................................... 9-189736

(51) Int. Cl.$^7$ .................................... C07C 69/30
(52) U.S. Cl. ............................ 560/227; 560/229
(58) Field of Search ..................... 560/227, 229

(56) References Cited

U.S. PATENT DOCUMENTS

| | | |
|---|---|---|
| 4,138,426 | 2/1979 | England . |
| 4,719,052 | 1/1988 | Ohsaka et al. . |
| 4,982,009 | 1/1991 | Hung . |
| 5,237,026 * | 8/1993 | Hung .................. 526/247 |
| 5,354,910 * | 10/1994 | Hung .................. 526/247 |

FOREIGN PATENT DOCUMENTS

| | | |
|---|---|---|
| 523017 | 1/1977 | (JP) . |
| 58-085832 | 5/1983 | (JP) . |
| 60-156632 | 8/1985 | (JP) . |
| 60-168711 | 9/1985 | (JP) . |
| 61-021457 | 1/1986 | (JP) . |
| 61-021458 | 1/1986 | (JP) . |
| 61-130254 | 6/1986 | (JP) . |
| 5503935 | 6/1993 | (JP) . |
| 9111420 | 8/1991 | (WO) . |

* cited by examiner

*Primary Examiner*—Robert Gerstl
(74) *Attorney, Agent, or Firm*—Birch, Stewart, Kolasch & Birch, LLP

(57) ABSTRACT

A fluorovinyl ether of the formula: $R^1CO(OCH_2CF_2CO)_k$—$(OCH_2CF_2CF_2)_m[OCF(CF_3)CF_2]_nOCF{=}CF_2$ wherein $R^1$ is an $C_1$–$C_8$ aliphatic or halogenated $C_1$–$C_8$ aliphatic group or an aromatic group which may optionally have at least one substituent, k is an integer of at least 0, m is an integer of at least 1, and n is an integer of at least 0.

5 Claims, No Drawings

FLUOROVINYL ETHER HAVING TERMINAL OXYGEN-CONTAINING FUNCTIONAL GROUP AND PROCESS FOR PREPARING THE SAME

BACKGROUND OF THE INVENTION

1. Field of the Invention

The present invention relates to a fluorovinyl ether having a terminal oxygen-containing functional group and a process for the preparation of the same. A fluorovinyl ether having a terminal oxygen-containing functional group is useful as a monomer component for the preparation of a fluoropolymer having an oxygen containing functional group.

SUMMARY OF THE INVENTION

JP-A-60-156632, JP-A-60-168711 and U.S. Pat. No. 4,138,426 disclose processes for the preparation of a fluorovinyl ether having a terminal alkoxycarbonyl group of the formula:
$CH_3OCOCF_2CF_2[OCF(CF_3)CF_2]_nOCF=CF_2$ using $CH_3OCOCF_2CF_2OCH_3$ as a starting material, and JP-A-5-503935 and U.S. Pat. No. 4,982,009 disclose processes for the preparation of a fluorovinyl ether having a terminal hydroxyl group of the formula:
$HOCH_2CF_2CF_2[OCF(CF_3)CF_2]_nOCF=CF_2$ by the reduction of the above fluorovinyl ether having a terminal alkoxycarbonyl group with sodium borohydride.

JP-A-52-3017, JP-A-58-85832, JP-B-61-21457 and JP-B-61-21458 disclose processes for the preparation of a fluorovinyl ether having a terminal alkoxycarbonyl group: $CH_3OCOCF_2CF_2CF_2O—CF=CF_2$, and a fluorovinyl ether having a terminal hydroxyl group: $HOCH_2CF_2CF_2CF_2OCF=CF_2$.

The above processes have their own problems. For example, the processes disclosed in JP-A-60-156632, etc. have a drawback that it is difficult to obtain the starting material, while the processes disclosed in JP-A-52-3017, etc. necessitate a number of reaction steps. In addition, the both processes should use $SO_3$ the handling of which is difficult.

SUMMARY OF THE INVENTION

One object of the present invention is to provide a novel process for the preparation of a fluorovinyl ether having a terminal oxygen-containing group, which does not suffer from the problems of the above conventional processes.

Another object of the present invention is to provide a fluorovinyl ether having a new chemical structure which has not been able to be prepared by the conventional processes.

Firstly, the present invention provides a fluorovinyl ether of the formula:

$$R^1CO(OCH_2CF_2CO)_k(OCH_2CF_2CF_2)_m[OCF(CF_3)CF_2]_nOCF=CF_2 \qquad (I)$$

wherein $R^1$ is an aliphatic or halogenated aliphatic group having 1 to 8 carbon atoms or an aromatic group which may optionally have at least one substituent, k is an integer of at least 0, m is an integer of at least 1, and n is an integer of at least 0, preferably k is an integer of 0 to 10, m is an integer of 1 to 5, and n is an integer of 0 to 10.

Secondly, the present invention provides a process for the preparation of a fluorovinyl ether having a terminal oxygen-containing group of the formula (I), comprising the steps of:

reacting hexafluoropropeneoxide with an acid fluoride of the formula:

$$R^1CO(OCH_2CF_2CO)_k(OCH_2CF_2CF_2)_{m-1}OCH_2CF_2COF \qquad (II)$$

wherein $R^1$, k and m are the same as defined above, in the presence of a metal fluoride to obtain an acid fluoride of the formula:

$$R^1CO(OCH_2CF_2CO)_k(OCH_2CF_2CF_2)_m[OCF(CF_3)CF_2]_nOCF(CF_3)COF \qquad (III)$$

wherein $R^1$, k, m and n are the same as defined above, pyrolyzing the acid fluoride of the formula (III) as such, or after the conversion of the acid fluoride of the formula (III) to a corresponding carboxylate salt through a reaction with a metal salt, to obtain the compound of the formula (I).

Thirdly, the present invention provides a process for the preparation of a fluorovinyl ether having a terminal hydroxyl group of the formula:

$$H(OCH_2CF_2CO)_{k'}(OCH_2CF_2CF_2)_m[OCF(CF_3)CF_2]_nOCF=CF_2 \qquad (IV)$$

wherein m and n are the same as defined above, and k' is an integer of 0 to k, comprising the step of converting the terminal acyloxy group of a fluorovinyl ether having a terminal oxygen-containing functional group of the formula (I) to a hydroxyl group by hydrolysis to obtain the compound of the formula (IV).

The process of the present invention uses an acid fluoride of the formula (II) as a starting material. When this acid fluoride is used as a starting material, the fluorovinyl ether of the present invention can be prepared from a readily available starting material in a fewer reactions steps. An acyl group functions as a protecting group of a hydroxyl group, since the hydroxyl group reacts with a fluorovinyl ether group.

DETAILED DESCRIPTION OF THE INVENTION

The acid fluoride used as a starting material in the process of the present invention, which is represented by the formula (II), is preferably a halogenated carboxylic acid ester-acid fluoride which is prepared by reacting a halogenated carboxylic acid salt with 2,2,3,3-tetrafluorooxetane as disclosed in JP-A-61-130254.

The group $R^1$ having the larger number of halogen atoms is more preferable. Thus, preferable examples of the group $R^1$ are a perfluoroalkyl group having 1 to 8 carbon atoms, ω-H-perfluoroalkyl group having 1 to 8 carbon atoms, ω-Cl-perfluoroalkyl group having 1 to 8 carbon atoms, and $Cl(CF_2CFCl)_pCF_2—$ wherein p is 1, 2 or 3, etc.

Examples of the aromatic group are phenyl, 1-naphthyl, 2-naphthyl, 2-furyl, 3-furyl, 2-thienyl, 3-thienyl, etc., and examples of substituents present on the aromatic rings are a methyl group, a methoxy group, an acetyl group, a nitro group, a cyano group, a fluorine atom, a chlorine atom, a bromine atom, etc.

The reaction between hexafluoropropeneoxide (hereinafter referred to as "HFPO") and the acid fluoride of the formula (II) may be carried out by a process which is used for reacting a general acid fluoride and HFPO.

As a solvent, any solvent that does not react with the acid fluoride (II) can be used. Glymes are preferable. The amount of a solvent is not limited. Usually, the amount of a solvent is 0.5 to 5 times the volume of the acid fluoride (II).

The kind of a metal fluoride is not limited. Preferable examples of metal fluorides are alkali metal fluorides such as otassium fluoride and cesium fluoride.

The amount of a metal fluoride is not limited either. referably, the metal fluoride is used in an amount of 0.9 to 1.2 moles per one mole of the acid fluoride (II).

The reaction temperature is not critical. Usually, the reaction temperature is maintained in the range between −60° C. and −20° C. when HFPO is added.

In an optional step, an acid fluoride of the formula (III), which has been formed by the reaction of the acid fluoride (II) and HFPO, maybe converted to a carboxylate salt by various methods, for example, neutralization with an alkali or a carbonate salt. In particular, the transfer reaction of an acid fluoride moiety with a metal salt is preferable for avoiding the hydrolysis of the carboxylate ester moiety.

The kind of a solvent used in the step for forming the carboxylate salt is not limited. Glymes are preferably used like in the reaction with HFPO. The amount of a solvent is not limited either. Preferably, a solvent is used in an amount of 0.5 to 5 times the volume of the acid fluoride of the formula (III).

A metal salt may be any one of organic and inorganic salts of oxyacids. In particular, salts of aliphatic carboxylic acids having 1 to 8 carbon atoms, salts of halogenated aliphatic carboxylic acids having 1 to 8 carbon atoms or salts of aromatic carboxylic acids having 6 to 8 carbon atoms (in the aromatic moiety) are preferable. The kind of a metal in the metal salt is not limited. Alkali metals are preferable.

The amount of a metal salt is at least 0.9 mole, preferably 1.0 to 1.2 moles, per one mole of the acid fluoride (III).

When the acid fluoride (III) as such or its carboxylate salt is pyrolyzed, a solvent is not always used. When a solvent is used, one that does not react with the fluorovinyl ether is used. Glymes are preferable, like in the previous reaction.

The amount of a solvent is not limited. After the solvent and a by-produced acid fluoride are removed from the reaction mixture from the previous reaction by distillation to condense the reaction mixture, the pyrolysis is preferably carried out in the presence of a solvent of 0.1 to 1 time the volume of the acid fluoride or carboxylate salt for easy removal of the solvent from the product.

The pyrolysis is carried out usually at a temperature in the range between 80° C. and 300° C., preferably in a solvent such as a glyme at a temperature in the range between 100°C. and 140° C.

The method of hydrolysis is not limited when the terminal group is converted to a hydroxyl group by removing the acyl group with hydrolysis. Preferably, the fluorovinyl ether (I) is dissolved in a halogen-containing solvent in which the fluorovinyl ether as a substrate can be dissolved, and the solvent is shaken together with an alkali.

The kind of an alkali to be used is not limited. Preferably, aqueous solutions of hydroxides or carbonates of alkali metals are used. If the alkali is used in an excessive amount, the excess alkali undesirably reacts with the vinyl ether moiety. Usually, the alkali is used in an amount of 1.0 to 1.2 equivalents per one equivalent of the ester-fluorovinyl ether (I).

The reaction temperature is not limited. A temperature around room temperature is preferable.

The process of the present invention can prepare a fluorovinyl ether having a terminal acyloxy group or a terminal hydroxyl group in a short reaction route.

The terminal acyl group can be removed without the destruction of a fluorovinyl ether structure, since the hydrolysis of a carboxylate ester is easy.

Furthermore, it is possible to obtain a polymer having a terminalhydroxyl groupbypolymerizinga fluorovinyl ether having a terminal acyloxy group and then removing the acyl group.

The polymer obtained by the above method, or a polymer having a terminal hydroxyl group obtained by polymerizing a fluorovinyl ether having a terminal hydroxyl group can be used as an adhesive for fluorine-containing polymers, a tackifier, a composite material comprising fluorine-containing polymers, and an adhesive or a tackifier for such a composite material.

A polymer, which is obtained by polymerizing a fluorovinyl ether having a 2,2,3,3-tetrafluoropropionyl group as an acyl group, can be used as a sustained-release herbicide.

EXAMPLES

The present invention will be illustrated by the following examples.

Example 1

1.1) Synthesis of $CF_3COOCH_2CF_2COF$

Sodium trifluoroacetate (27.2 g, 0.2 mole) and glyme (1,2-dimethoxyethane) (100 ml) were charged in a two-necked 200 ml flask equipped with a stirrer. Then, 2,2,3,3-tetrafluorooxetane (27 g, 0.21 mole) was added while stirring and cooling on an ice bath. The ice bath was removed, and the mixture in the flask was allowed to warm up to room temperature, and stirred at room temperature for further 3 hours.

The solvent was evaporated off at a bath temperature of 90° C. under atmospheric pressure. Then, the product was distilled at bath temperature in the range between 50°C. and 80° C. under a reduced pressure of 126 mmHg. Boiling temperature, 47–48°C./126 mmHg.

The main fraction (34 g) was analyzed by $^1$H-NMR and $^{19}$F-NMR. The product was found to be a mixture of 40.0 wt. % of the above entitled compound and the rest of glyme. Yield, 30%.

$^1$H-NMR (glyme): δ 5.20 (2H, t, J=13 Hz).

$^{19}$F-NMR (glyme): +18.7 (1F, t, J=8 Hz), −76.0 (3F, s), −113.9 (2F, m) ppm (external standard: $CFCl_3$).

1.2) Synthesis of $CF_3COOCH_2CF_2CF_2[OCF(CF_3)CF_2]_n OCF(CF_3)COF$

Cesium fluoride (9.1 g, 60 mmoles), the main fraction (34 g, 60 mmoles) from the step 1.1) and diglymie (50 ml) were charged in a four-necked 200 ml flask equipped with a stirrer, a gas-inlet tube, a low-temperature thermometer, and a dry-iced condenser. The internal temperature was lowered to −50° C. on a dry ice-methanol bath while stirring, and then HFPO (30 g, 180 mmoles) was added through the gas-inlet tube at a rate such that the internal temperature did not exceed −30° C. (over 10 minutes) After the addition of HFPO, the mixture was stirred at −50° C. for 1 hour. Thereafter, the dry ice-methanol bath was removed, and the reaction mixture was allowed to warm up to room temperature (over 30 minutes). Then, the mixture was stirred at room temperature overnight.

The product was distilled from the reaction mixture at a bath temperature in the range between 60° C. and 100° C. under a reduced pressure of 50 mmHg. Boiling temperature, 40–74°C./50 mmHg.

The main fraction (18 g) was analyzed by $^1$H-NMR and $^{19}$F-MR. The product was found to be a mixture of 40.0 wt. % of the above entitled compound and the rest of diglyme. The average number of added HFPO in the entitled compound was 2.5 (n=1.5). Yield, 19%.

$^1$H-NMR (diglyme): δ 5.0–5.6 (m).

$^{19}$F-NMR (diglyme):

Compound in which n=0: +25.3 (1F, br.s), −74.8 (3F, s), −82.6 (1F, br.d, J=152 Hz), −84.5 (3F, s), −89.9 (1F, d, J=152 Hz), −123.7 (2F, m), −131.7 (1F, m) ppm (external standard: $CFCl_3$).

Compound in which n=1: +25.1 (1F, br.s), −74.8 (3F, s), −79.9 (1F, br.d, J=158 Hz), −81.2 (3F, br.s), −84.6 (3F, s), −86.1 (2F, br.s), −87.0 (1F, br.d, J=158 Hz), −123.7 (2F, m), −131.7 (1F, m), −146.1 (1F, m) ppm (external standard: $CFCl_3$).

1.3) Synthesis of $CF_3COOCH_2CF_2CF_2[OCF(CF_3)CF_2]_nOCF=CF_2$

The HFPO-added acid fluoride obtained in the step 1.2) (10 mmoles), diglyme (5 ml) and sodium acetate (0.82 g, 10 mmoles) were charged in a 50 ml egg-plant type flask, and stirred at room temperature for 6 hours. The solvent and by-produced acetyl fluoride were distilled off at a bath temperature of 70° C. under reduced pressure of 15 mmHg, and then the bath temperature was raised to 120° C. to carry out the pyrolysis and the distillation of the product. The main fraction (3.5 g) was analyzed by $^1$H-NMR and $^{19}$F-NMR. The product was found to be a 15 wt. % solution of the above entitled compound in diglyme, n was 1.4 on the average, and a content of the entitled compound in the product was 0.2 in a molar ratio. Yield, 2%.

Compound in which n=0:
$^1$H-NMR (diglyme): δ 5.03 (2H, t, J=13 Hz).
$^{19}$F-NMR (diglyme): −74.8 (3F, s), −90.2 (2F, s), −118.2 (1F, dd, J=88 Hz, 66 Hz), −124.7 (2F, m), −125.9 (1F, dd, J=110 Hz, 88 Hz), −137.6 (1F, dd, J=110 Hz, 66 Hz) ppm (external standard: $CFCl_3$).

Compound in which n=1:
$^1$H-NMR (diglyme): δ 5.01 (2H, t, J=13 Hz).
19F-NMR (diglyme): −74.8 (3F, s), −81.8 (3F, s), −86.6 (2F, br.s), −87.0 (2F, m), −117.8 (1F, dd, J=87 Hz, 66 Hz), −124.6 (2F, q, J=12 Hz), −125.4 (1F, dd, J=112 Hz, 87 Hz), −138.0 (1F, dd, J=112 Hz, 66 Hz), −146.6 (1F, m) ppm (external standard: $CFCl_3$).

Example 2

2.1) Synthesis of $HCF_2CF_2COOCH_2CF_2COF$

Sodium 2,2,3,3-tetrafluoropropionate (338 g, 2.0 moles) and glyme (1.5 liters) were charged in a four-necked 2 liter flask equipped with a stirrer, and dissolved at 35° C. After cooling to room temperature, 2,2,3,3-tetrafluorooxetane (277 g, 2.1 moles) was added over 15 minutes while stirring, followed by stirring at room temperature for 5 hours. During this period, a slight amount of heat was generated, and the whole reaction mixture temporally became a slurry.

The solvent was evaporated off at a bath temperature of 110–120° C. under atmospheric pressure. Then, the product was distilled at a bath temperature in the range between 100° C. and 120° C. under a reduced pressure of 10 mmHg. Boiling temperature, 41°C./10 mmHg.

The main fraction (302 g) was analyzed by $^1$H-NMR and $^{19}$F-NMR. The product was found to be a mixture of 74.5 wt. % of the above entitled compound and the rest of glyme. Yield, 44%.

$^1$H-NMR (glyme): δ 5.16 (2H, t, J=13 Hz), 6.47 (1H, tt, J=53 Hz, 4 Hz).

$^{19}$F-NMR (glyme): +18.9 (1F, t, J=8 Hz), −114.0 (2F, m), −124.2 (2F, m), −138.5 (2F, dm, J=54 Hz) ppm.

2.2) Synthesis of $HCF_2CF_2COOCH_2CF_2CF_2[OCF(CF_3)CF_2]_n-OCF(CF_3)COF$

Cesium fluoride (133 g, 0.88 mole), the main fraction (302 g, 0.88 mole) from the step 2.1) and diglymie (0.5 liter) were charged in a four-necked 1 liter flask equipped with a stirrer, a gas-inlet tube, a low-temperature thermometer, and a dry-iced condenser. The internal temperature was lowered to −50° C. on a dry ice-methanol bath while stirring, and then HFPO (290 g, 1.75 moles) was added through the gas-inlet tube at a rate such that the internal temperature did not exceed −30° C. (over 45 minutes) After the addition of HFPO, the mixture was stirred at −50°C. for 1 hour. Thereafter, the dry ice-methanol bath was removed, and the reaction mixture was allowed to warm up to room temperature (over 80 minutes). Then, the mixture was stirred at room temperature overnight.

The solvent was distilled off from the reaction mixture at a bath temperature of 70° C. under reduced pressure of 2 mmHg. Then, the bath temperature was gradually raised to 140° C., and the product was distilled. Boiling temperature, 50–94° C./2 mmHg.

The main fraction (394 g) was analyzed by $^1$H-NMR and $^{19}$F-NMR. The product was found to be a mixture of 85.3 wt. % of the above entitled compound and the rest of diglyme. The average number of added HFPO in the entitled compound was 2.01 (n=1.01). Yield, 65%.

$^1$H-NMR (diglyme): δ 4.9–5.2 (m), 6.34 (1H, tm, J=53 Hz).

$^{19}$F-NMR (diglyme):

Compound in which n=0: +24.6 (1F, br.s), −82.7 (1F, dd, J=147 Hz, 22 Hz), −83.8 (3F, s), −90.7 (1F, d, J=147 Hz), −124.8 (2F, m), −125.4 (2F, m), −132.3 (1F, m), −139.5 (2F, dm, J=51 Hz) ppm (external standard: $CFCl_3$).

Compound in which n=1: +24.8 (1F, br.s), −79.9 (1F, br.d, J=141 Hz), −81.8 (3F, br.s), −83.9 (3F, s), −85.0 (2F, br.s), −87.3 (1F, br.d, J=141 Hz), −124.8 (2F, m), −125.4 (2F, m), −132.3 (1F, m), −139.5 (2F, dm, J=51 Hz), −146.5 (1F, m) ppm (external standard: $CFCl_3$).

2.3) Synthesis of $HCF_2CF_2COOCH_2CF_2CF_2[OCF(CF_3)CF_2]_nOCF=CF_2$

The HFPO-added acid fluoride obtained in the step 2.2) (0.59 mole), diglyme (150 ml) and sodium acetate (49 g, 0.60 mole) were charged in a four-necked 1 liter flask equipped with a stirrer, and stirred at room temperature for 3 hours. The solvent and by-produced acetyl fluoride were distilled off at a bath temperature of 70° C. under reduced pressure of 10 mmHg, and then the mixture was heated at a bath temperature of 120° C. under atmospheric pressure for 5 hours.

The product was distilled from the reaction mixture at bath temperatures of 70° C., 100° C. and 140° C. under reduced pressure of 2 mmHg. The boiling points, masses, averaged n, ratios and yields of the fractions are shown in Table 1. Total yield, 9.4%.

TABLE 1

| Bath temp. (° C.) | Boiling temp. (° C.) | Mass (g) | Weight % of product | n on average | Molar ratio of desired compound in product | Yield (%) |
|---|---|---|---|---|---|---|
| ca. 70 | 37–51 | 119 | 64.0 | 0.7 | 0.25 | 6.8 |
| ca. 100 | 61–71 | 54 | 95.5 | 1.2 | 0.10 | 1.6 |
| ca. 140 | 84–98 | 49 | 98.4 | 2.3 | 0.09 | 1.0 |

A part (112 g) of the first fraction was dissolved in perfluorohexane (200 ml), and washed with water (each 300 ml) seven times, followed by drying over anhydrous magnesium sulfate, and filtration.

Perfluorohexane was distilled off from the filtrate under atmospheric pressure, and the filtrate was fractionated with a Vigreu tube having a length of 15 cm under reduced pressure of 3 mmHg. The four fractions were recovered. Their boiling temperatures, masses, averaged n and molar ratios of desired products are shown in Table 2.

TABLE 2

| Bath temp. (° C.) | Boiling temp. (° C.) | Mass (g) | n on average | Molar ratio of desired compound |
|---|---|---|---|---|
| ca. 60 | 26–30 | 2.5 | 0.09 | 0.41 |
| ca. 60 | 26–30 | 6.0 | 0.16 | 0.33 |
| ca. 70 | 40–44 | 25.2 | 1.00 | 0.33 |
| Still residue | — | 18.5 | 1.24 | 0.15 |

Compound in which n=0:
$^1$H-NMR (neat): δ 4.92 (2H, t, J=13 Hz), 6.10 (1H, tt, J=53 Hz, 4 Hz).
$^{19}$F-NMR (neat) −90.7 (2F, s), −117.5 (1F, dd, J=88 Hz, 66 Hz), −125.2 (1F, dd, J=110 Hz, 88 Hz), −125.8 (2F, m), −125.9 (2F, m), −138.2 (1F, dd, J=110 Hz, 66 Hz), −139.8 (2F, dqui, J=53 Hz, 6 Hz) (external standard: CFCl$_3$).
Compound in which n=1:
$^1$H-NMR (neat): δ 4.90 (2H, t, J=13 Hz), 6.10 (1H, tt, J=53 Hz, 4Hz).
$^{19}$F-NMR (neat): −82.4 (3F, s)) −85.9 (2F, m), −86.9 (2F, br.s), −117.1 (1F, dd, J=87 Hz, 66 Hz), −124.7 (1F, dd, J=112 Hz, 87 Hz), −125.7 (2F, q, J=12 Hz), −125.9 (2F, m), −138.6 (1F, dd, J=112 Hz, 66 Hz), −139.8 (2F, dsex, J=53 Hz, 6 Hz) −147.0 (1F, m) ppm (external standard: CFCl$_3$).

Example 3
Synthesis of HOCH$_2$CF$_2$CF$_2$[OCH(CF$_3$)CF$_2$]$_n$OCF=CF$_2$

The fluorovinyl ether obtained in the step 2.3) of Example 2 (5.4 g, 10 mmoles; n=1.00 on the average) was dissolved in perfluorohexane (10 g). To this solution, an aqueous solution (10 g) of sodium hydroxide (0.42 g, 10.5 mmoles) was added, and the mixture was vigorously shaken three times. The lower organic layer was washed with water (each 20 ml) twice and dried over anhydrous magnesium sulfate, followed by filtration. Then, perfluorohexane was evaporated off under atmospheric pressure. According to $^{19}$F-NMR analysis, the net yield of the above entitled compound was 3.8 g (94%).

$^1$H-NMR (C$_6$F$_{14}$): δ 4.02 (2H, t, J=14 Hz), 4.26 (1H, br.s).
$^{19}$F-NMR (C$_6$F$_{14}$): −82.6 (3F, s), −85–87 (1F, m), −86.0 (2F, br.s), −87–89 (1F, m), −117.6 (1F, m), −124.9 (1F, m), −128.8 (2F, m), −138.8 (1F, m), −147.4 (1F, m) ppm (external standard: CFCl$_3$).

What is claimed is:
1. A fluorovinyl ether of the formula:

    OCF=CF$_2$      (I)

wherein R$^1$ is a halogenated aliphatic group having 1 to 8 carbon atoms, k is an integer of at least 0, m is an integer of at least 1, and n is an integer of at least 0.

2. The fluorovinyl ether according to claim 1, wherein k is an integer of 0 to 10, m is an integer of 1 to 5, and n is an integer of 0 to 10.

3. The fluorovinyl ether according to claim 1, wherein R$^1$ is a perfluoroalkyl group having 1 to 8 carbon atoms, a ω-H-perfluoroalkyl group having 1 to 8 carbon atoms, a ω-Cl-perfluoroalkyl group having 1 to 8 carbon atoms, or a group of the formula: Cl(CF$_2$CFCl)$_p$CF$_2$— wherein p is 1, 2 or 3.

4. A process for the preparation of a fluorovinyl ether having a terminal oxygen-containing group of the formula (I):

    OCF=CF$_2$      (I)

wherein R$^1$ is a halogenated aliphatic group having 1 to 8 carbon atoms, k is an integer of at least 0, m is an integer of at least 1, and n is an integer of at least 0, comprising the steps of:

reacting hexafluoropropeneoxide with an acid fluoride of the formula:

      (II)

wherein R$^1$, k and m are the same as defined above, in the presence of a metal fluoride to obtain an acid fluoride of the formula:

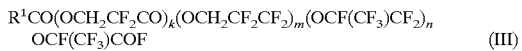
    OCF(CF$_3$)COF      (III)

wherein R$^1$, k, m and n are the same as defined above; and pyrolyzing after the conversion of the acid fluoride of the formula (III) to a corresponding carboxylate salt through a reaction with a metal salt of an organic acid.

5. The process according to claim 4, wherein said metal fluoride is cesium fluoride.

* * * * *